United States Patent
Shaw

(10) Patent No.: US 6,726,683 B1
(45) Date of Patent: Apr. 27, 2004

(54) ELECTRICALLY HEATED SURGICAL CUTTING INSTRUMENT

(76) Inventor: Robert F. Shaw, 800 Wilshire Blvd., Los Angeles, CA (US) 90017

( * ) Notice: Subject to any disclaimer, the term of this patent is extended or adjusted under 35 U.S.C. 154(b) by 1,826 days.

(21) Appl. No.: 05/730,221

(22) Filed: Oct. 6, 1977

Related U.S. Application Data

(62) Division of application No. 05/534,756, filed on Dec. 2, 1974, now Pat. No. 4,089,336, which is a continuation of application No. 05/063,645, filed on Aug. 13, 1970, now abandoned, which is a continuation of application No. 04/681,737, filed on Nov. 9, 1967, now abandoned.

(51) Int. Cl.[7] ............................................. A61B 17/38
(52) U.S. Cl. ......................... 606/31; 219/233; 219/241
(58) Field of Search .................. 128/303 R, 303.1, 128/303.13, 303.14, 1 R, 404–406; 30/140; 219/233, 235–241, 251, 210, 227–231, 499, 504, 505, 512; 606/27–31

(56) References Cited

U.S. PATENT DOCUMENTS

| | | | | |
|---|---|---|---|---|
| 956,604 A | * | 5/1910 | Savoy ..................... 219/233 X |
| 958,753 A | * | 5/1910 | Meyer ............... 128/303.14 X |
| 1,083,386 A | * | 1/1914 | Chapman ..................... 30/140 |
| 1,713,970 A | * | 5/1929 | Lowry et al. .......... 128/303.14 |
| 1,735,271 A | * | 11/1929 | Groff .................... 128/303.14 |
| 1,794,296 A | * | 2/1931 | Hyams .................. 128/303.14 |
| 1,930,214 A | * | 10/1933 | Wappler ................ 128/303.14 |
| 1,947,857 A | * | 2/1934 | Khebs .......................... 219/21 |
| 2,012,938 A | * | 9/1935 | Beuoy .................... 128/303.14 |
| 2,623,977 A | * | 12/1952 | Weiskopf ..................... 30/140 |
| 2,763,762 A | * | 9/1956 | Jepson ................. 128/303.1 X |
| 2,795,697 A | * | 6/1957 | Nagel ..................... 217/499 X |
| 2,863,036 A | * | 12/1958 | Mitchell et al. ............... 30/140 |
| 2,866,068 A | * | 12/1958 | Bernstein ...................... 219/21 |
| 2,917,614 A | * | 12/1959 | Caliri et al. ......... 128/303.1 X |
| 2,994,053 A | * | 7/1961 | De Waard ..................... 338/18 |
| 3,024,342 A | * | 3/1962 | Birnbach ...................... 219/21 |
| 3,060,298 A | * | 10/1962 | Swanson ...................... 219/20 |
| 3,207,159 A | * | 9/1965 | Tateisi ..................... 128/303.1 |
| 3,234,356 A | * | 2/1966 | Babb ....................... 128/303.1 |
| 3,316,765 A | * | 5/1967 | Trolander .................... 73/362 |
| RE26,276 E | * | 10/1967 | Hirschhorn .............. 128/303.1 |
| 3,400,252 A | * | 9/1968 | Hayakawa ................... 219/504 |
| 3,414,705 A | * | 12/1968 | Maroux ...................... 219/210 |
| 3,502,080 A | * | 3/1970 | Hirschhorn .............. 128/303.1 |
| 3,526,750 A | * | 9/1970 | Siegel ......................... 219/233 |
| 3,584,190 A | * | 6/1971 | Marcoux ..................... 219/233 |
| 3,826,263 A | * | 7/1974 | Cage et al. ............. 128/303.1 |
| 4,089,336 A | * | 5/1978 | Cage et al. ............. 128/303.1 |

FOREIGN PATENT DOCUMENTS

| | | | | |
|---|---|---|---|---|
| GB | 605328 | * | 7/1948 | ................... 30/140 |
| GB | 615027 | * | 12/1948 | ................... 30/140 |
| GB | 641034 | * | 8/1950 | ............ 128/303.14 |
| IT | 550456 | * | 10/1956 | ................... 30/140 |

OTHER PUBLICATIONS

Board of Patent Appeals and Interferences, Decision in Interference No. 100,775, Aug. 5, 1996.
Board of Patent Appeals and Interferences, Decision in Application No. 07/117,393, Mar. 27, 2003.

* cited by examiner

Primary Examiner—Michael H. Thaler
(74) Attorney, Agent, or Firm—Fish & Neave

(57) ABSTRACT

Surgical cutting instrument includes an electrically heated cutting edge and an automatic control system for maintaining the cutting edge at a constant high temperature for sterilizing the blade, cutting tissue, and cauterizing the incised tissue to reduce hemorrhage from the cut surfaces of the tissues (hemostasis).

28 Claims, 1 Drawing Sheet

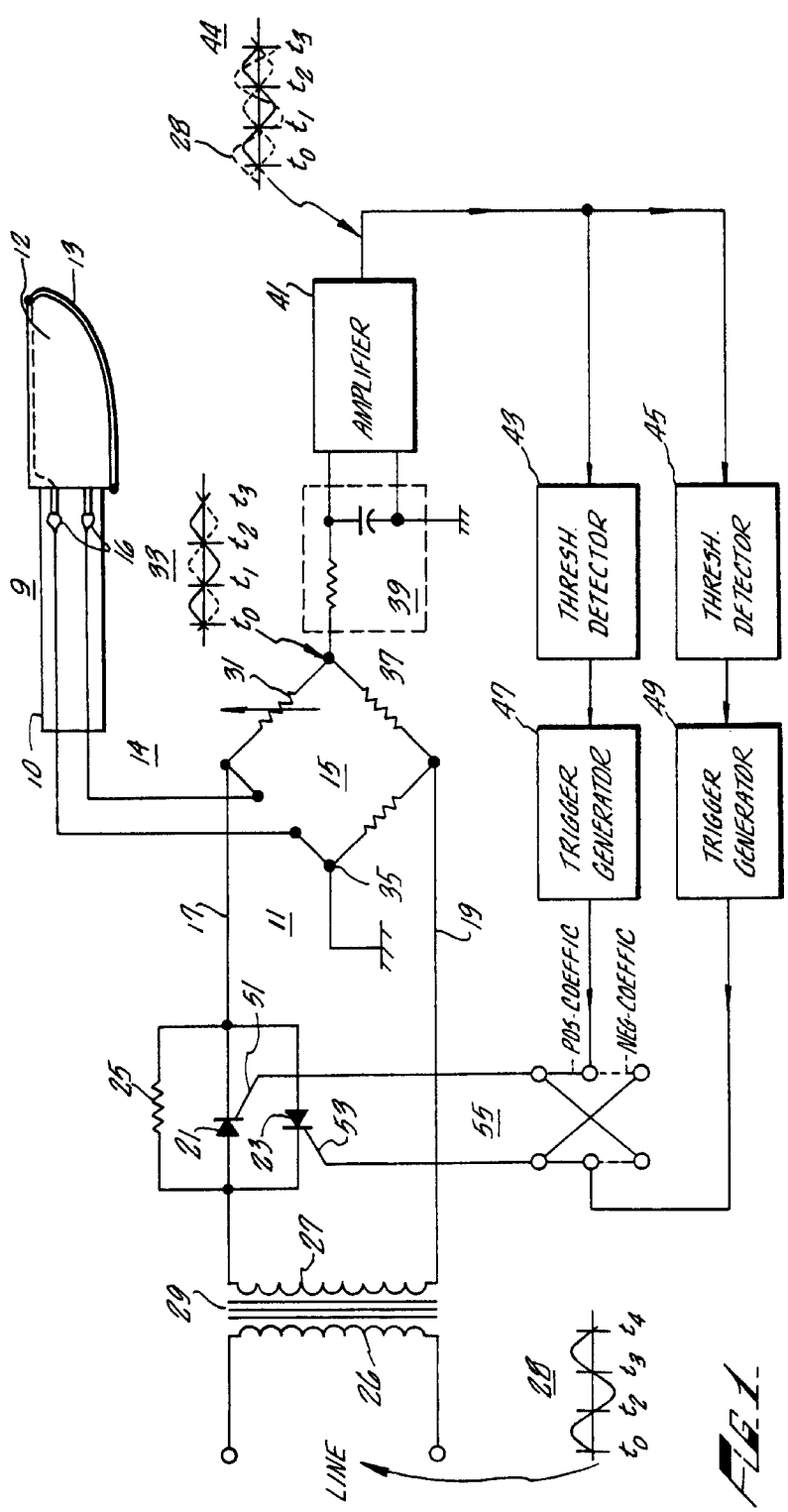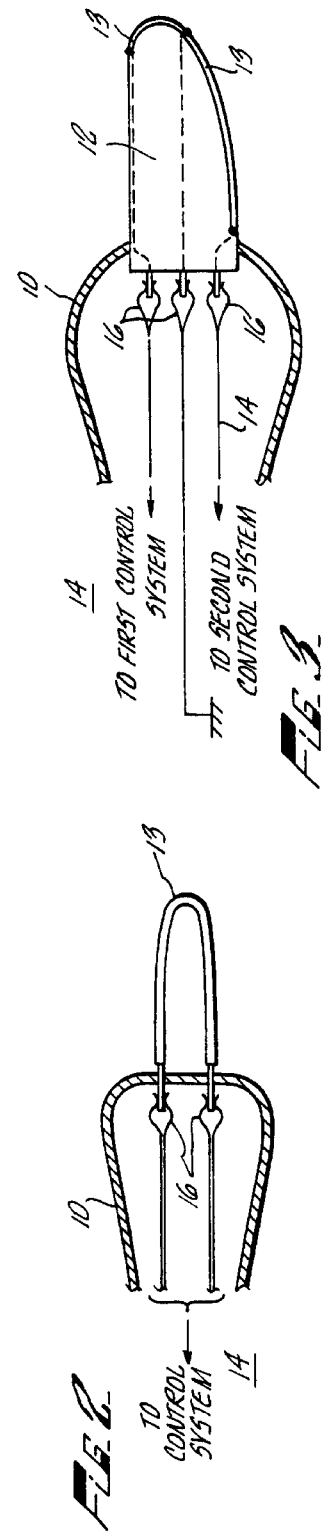

ELECTRICALLY HEATED SURGICAL CUTTING INSTRUMENT

RELATED APPLICATIONS

This application is a division application of U.S. patent application Ser. No. 05/534,756 filed Dec. 2, 1974, now U.S. Pat. No. 4,089,336, which is a continuation of U.S. patent application Ser. No. 05/063,645 filed Aug. 13, 1970, now abandoned, which is a continuation of U.S. patent application Ser. No. 04/681,737 filed Nov. 9, 1967, now abandoned.

BACKGROUND OF THE INVENTION

The control of bleeding during surgery accounts for a major portion of the total time involved in an operation. The bleeding that occurs when tissue is incised obscures the surgeon's vision, reduces his precision and often dictates slow and elaborate procedures in surgical operations. Each bleeding vessel must be grasped in pincer-like clamps to stop the flow of blood and the tissue and vessel within each clamp must then be tied with pieces of fine thread. These ligated masses of tissue die and decompose and thus tend to retard healing and promote infection.

SUMMARY OF THE INVENTION

Accordingly, the present invention provides a surgical cutting instrument having a cutting edge which is electrically heated to a constant high temperature for sterilizing the blade, cutting the tissue and cauterizing the surfaces of the incision, thereby allowing surgery to be more rapidly performed. This is accomplished in accordance with the illustrated embodiment of this invention by providing an electrically heated element disposed as the cutting edges of he blade and by providing a control system witch maintains the cutting edge at a high substantially constant temperature during its use. The hot cutting edge according to the present invention decreases the amount of tissue that is damaged and reduces the tendency of the instrument to stick to the heated tissue in the incision. The material used in the electrically heated cutting edge has a negative temperature coefficient of resistance to insure that electrical power applied to the cutting edge is dissipated primarily in the regions thereof which tend to be cooled by contact with tissue. The temperature at which the cutting edge of the blade is maintained depends upon such factors as the nature of the tissue to be cut, the speed of cutting desired, the degree of tissue coagulation desired, and the non-adherence of the blade to the incised tissue and generally is maintained between 300°–1000° Centigrade for typical incisions. The instantaneous temperature of the cutting edge is monitored by measuring the resistance of the heating element itself or through the use of thermocouple elements disposed in the blade near the cutting edge, and the monitoring signal thus derived controls the power applied to the heating element. The handle of the cutting instrument is thermally insulated from the blade to permit comfortable use of the instrument and the handle and blade with its electrically heated cutting edge are detachable for easy replacement and interchangeability with blade, scoops and cutting edge of various shapes and sizes determined by the nature of the incision to be made and the tissue to be cut.

DESCRIPTION OF THE DRAWING

FIG. 1 is a schematic diagram showing the cutting instrument and the temperature control system therefor, according to the preferred embodiment of the present invention, and FIGS. 2 and 3 are pictorial views of other embodiments of cutting instruments according to the present invention for use with circuitry as shown in FIG. 1.

DESCRIPTION OF THE PREFERRED EMBODIMENT

Referring now to FIG. 1 of the drawing, there is shown the surgical cutting instrument 9 connected to a temperature-measuring and power-controlling system 11. The cutting instrument 9 includes a thin ceramic card 12 in the desired shape of a surgical cutting blade which is detachable from the handle or holder 10. An electrically heated element 13 is disposed along the leading edge of the card 12 to form its cutting edge and is electrically connected to the control circuit through the cable 14 and the connectors 16. The element 13 may be a single filament attached to the edge of the card 12, for example, using conventional ceramic welding materials or may be a layer of electrically conductive material vapor-deposited along the edge of the card 12. Also, the heating element 13 may have sufficient cross-sectional area to be self-supporting as shown in FIG. 2, so that the blade 18 is formed entirely by the element 13 alone. The material used in the element 13 ideally should have a negative temperature coefficient of resistance so that as selected portions of the element cool when in contact with tissue, the resistance of such portions will increase and thereby localize the portions of the element 13 in witch additional power supplied by the control system will be dissipated. The temperature of the element may thus be maintained substantially constant over the entire length thereof as portions of the element 13 contact tissue. Suitable materials having negative temperature coefficients of resistance include silicon carbide, carbon, boron silicate and such semiconductor materials as silicon and germanium. Of course, material having a positive coefficient of resistance may also be used. However, when materials of this type are used, care should be taken to shape the element 13 so that substantially the entire length of the element 13 contacts tissue in use. This is required to prevent the additional power supplied by the control system 11 from being dissipated in the portions of the element which do not cool when in contact with tissue and, hence, which have higher resistance than the cooler portions. For cutting applications where it is not convenient to shape the element 13 so that its entire length is in contact with tissue each time it is used, the element 13 may consist of a plurality of electrically isolated elements 13 and 13', as shown in FIG. 3, with each of the elements 13 and 13', connected to a separate temperature measuring and power-controlling system of the type shown in FIG. 1.

The resistance of the element 13 is included in a bridge circuit 15 which is connected to receive alternating signal appearing on lines 17 and 19. The level of alternating signal appearing on lines 17 and 19 and, hence, the power applied to element 13 is determined by the conduction angles of the controlled rectifiers 21 and 23 which are connected in conduction opposition in parallel across the series resistor 25. Power is supplied to the control system 11 through the primary and secondary windings 26 and 27 of power input transformer 29. Alternating line signal 28 applied to the transformer 29 is stepped down typically to about 24 volts for the safety of the patient and the surgeon and the average current flow per half cycle of the alternating signal is determined in part by the series resistor 25 and by the conduction angle of a silicon-controlled rectifier 21, 23.

The operating temperatures the element 13 may be determined by adjusting one of the resistors, say resistor 31, in the bridge circuit 15. Any variation in the operating temperature of element 13 front a set value unbalances the bridge 15 and produces a control signal 33 across the diagonal terminals 35, 37 of the bridge circuit 15 which is either in phase or out of phase with the applied line signal, depending upon whether the operating temperature of the element is above or below the set value of operating temperature. A phase-shifting network 39 is connected to the output terminals of the bridge circuit 15 for applying the error signal 44 with respect to ground to the input of error amplifier 41 with a small amount of phase shift relative to the applied line signal 28. This provides control of the conduction angle of the controlled rectifiers 21, 23 over a greater portion of a half cycle of the applied line signal. The output of amplifier 41 is applied to the threshold detectors 43, 45 which respond to the amplified error signal attaining selected value slightly above and below zero. The threshold detectors 47 and 49 thus activate the trigger pulse generators 47 and 49 at the proper times in alternate half cycles of applied line signal 28 to apply conduction-initiating pulses to the gate electrodes 51, 53 of the controlled rectifiers 21, 23. Thus, increased conduction angle of the controlled rectifiers 21 and 23 increases the power applied to the element 13 to maintain the element at a preselected operating temperature as the element tends to cool down in contact with sin tissue. However, if the operating temperature of the element 13 should exceed the set value due, for example, to thermal overshoot upon removal of the element 13 from contact with skin tissue, the phase of the error signal 33 with respect to the applied line signal reverses. This causes the trigger pulse generators to supply conduction-initiating pulses to the gate electrodes of the controlled rectifiers 21, 23 during alternate half cycles when these rectifiers are back biased. This causes a decrease in the power delivered to the element 13 with a concomitant drop in its operating temperature to about the set value of operating temperature. When this occurs, the proper phase relationship between error signal and line signal is restored and power is again supplied to the element 13. Conversion of the control system 11 for operation with elements 13 having negative or positive temperature coefficients of resistance merely requires that the trigger pulses from the generators 47 and 49 be applied through reversing switch 55 to the proper controlled rectifier 21, 23 during the forward-biasing half cycle of line signal 28.

It should be apparent that other temperature control systems may also be used to maintain the operating temperature of the element 13 substantially constant at a preselected value. For example, a thermocouple sensor may be disposed on the card 12 in close proximity with the element 13 or a thermocouple element may ever be formed on element 13 using another material or dissimilar work function to form the thermocouple junction. The signal from such thermocouple may then be used to control the operating temperature of the element 13 by controlling the power supplied thereto.

What is claimed is:

1. An instrument for cutting, the instrument comprising:
   blade-shaped means of said instrument that has an edge which forms the cutting edge thereof; including
   means capable of being heated to elevate the temperature of the blade-shaped means in the region of the cutting edge, said means capable of being heated being in the region of said edge and having a physical parameter which varies as a function of temperature to increase power dissipation in response to selective cooling of regions along said edge for maintaining the temperature of said edge within said selected temperature range.

2. An instrument as in claim 1 wherein:
   said means elevates the temperature in the region of said cutting edge to within the range between 300° C. and 1000° C.

3. An instrument as in claim 1 wherein:
   said blade-shaped means is formed of a non-metallic material.

4. An instrument as in claim 1 wherein:
   said blade-shaped means includes a ceramic material.

5. An instrument as in claim 1 wherein:
   said blade-shaped means includes electrically insulative material; and
   said means capable of being heated elevates the temperature of said region in response to electrical signal applied thereto.

6. An instrument as in claim 1 comprising:
   circuit means capable of being heated connecting said means to a source of electrical power for controlling the flow of electrical current through said means to maintain the average operating temperature thereof within said range.

7. An instrument as in claim 1 wherein said edge is said means capable of being heated.

8. A hemostatic surgical cutting blade comprising:
   a cutting blade having a tissue-cutting edge; including
   means capable of being maintained at a selected temperature range in response to selective cooling of regions along said edge by reason of contact with tissue being cut such that said edge is also capable of being maintained at a selected temperature range.

9. A hemostatic surgical cutting blade as in claim 8 wherein:
   said means capable of being heated is capable of elevating the temperature in the region of said tissue-cutting edge to within the range between 300° C. and 1000° C.

10. A hemostatic surgical cutting blade as in claim 8 wherein:
    said cutting blade is formed of non-metallic material.

11. A hemostatic surgical cutting blade as in claim 8 wherein:
    said cutting blade includes a ceramic material.

12. A hemostatic surgical cutting blade as in claim 8 wherein said tissue-cutting edge is said means capable of being heated.

13. A surgical instrument for cutting tissue with simultaneous hemostasis, the instrument comprising:
    blade means having a tissue-cutting edge; including
    means capable of being heated in the region of said edge having a physical parameter which varies as a function of temperature to increase power dissipation in response to selective cooling of regions along said edge by reason of contact with tissue being cut such that said edge is capable of being maintained at a selected temperature range.

14. A surgical instrument as in claim 13 wherein:
    said means capable of being heated elevates the temperature in the region of said tissue-cutting edge to within the range between 300° C. and 1000° C.

15. A surgical instrument as in claim 13 wherein:
    said blade-shaped means is formed of non-metallic material.

16. A surgical instrument as in claim 13 wherein:
    said blade-shaped means includes a ceramic material.

17. A surgical instrument as in claim 13 wherein:

said blade-shaped means includes electrically insulative material; and said means capable of being heated elevates the temperature of said region in response to electrical signal applied thereto.

18. A surgical instrument as in claim 13 wherein:

circuit means connecting said means to a source of electrical power for controlling the flow of electrical current through said means to maintain the average operating temperature thereof within said range.

19. A surgical instrument as in claim 13 wherein said tissue-cutting edge is said means capable of being heated.

20. A surgical instrument or cutting tissue with simultaneous hemostasis, the instrument comprising:

blade means having a tissue-cutting portion; including means capable of selectively increasing power dissipation within region of the tissue being cut by said blade means.

21. A surgical instrument as in claim 20 wherein:

said means capable of being heated elevates the temperature in the region of the tissue being cut to within the range between 300° C. and 1000° C.

22. A surgical instrument as in claim 20 wherein said tissue-cutting edge is said means capable of being heated.

23. The method of surgically cutting tissue with simultaneous hemostasis comprising the steps of:

contacting tissue to be cut with a tissue-cutting edge which is at an elevated temperature; and increasing power dissipation in selected regions along the edge which are cooled upon contact with tissue for maintaining the temperature of the edge substantially within a selected operating range.

24. The method according to claim 23 wherein:

in the step of contacting tissue, the temperature of the tissue-cutting edge is elevated to within the range between 300° C. and 1000° C.

25. The method according to claim 23 wherein:

in the step of contacting tissue, the temperature of the tissue-cutting edge is elevated in response to applied electrical signal.

26. The method according to claim 23 wherein:

in the step of increasing power dissipation, a flow of electrical current from a source of electrical signal is controlled along the tissue-cutting edge to maintain the average operating temperature thereof within said range.

27. A method of cutting comprising the steps of:

contacting a material to be cut with a cutting edge which is at an elevate temperature; and increasing power dissipation in selected regions along the edge which are cooled upon contact with said material to be cut for maintaining the temperature of the edge substantially within a selected operating range.

28. The method of cutting as in claim 27 wherein in the step of increasing power dissipation, a flow of electrical current from a source of electrical signal is controlled along the cutting edge to maintain the average operating temperature thereof within said range.

\* \* \* \* \*

UNITED STATES PATENT AND TRADEMARK OFFICE
CERTIFICATE OF CORRECTION

PATENT NO. : 6,726,683 B1
DATED : April 27, 2004
INVENTOR(S) : Robert F. Shaw

It is certified that error appears in the above-identified patent and that said Letters Patent is hereby corrected as shown below:

<u>Title page,</u>
Item [22], Filed:, "1977" should be -- 1976 --;
Item [57], ABSTRACT,
Line 1, "Surgical" should be -- A surgical --.

<u>Column 2,</u>
Line 27, "witch" should be -- which --;
Line 48, "13', connected" should be -- 13' connected --;
Line 66, after "temperatures" should be inserted -- of --.

<u>Column 3,</u>
Line 16, "value" should be -- values --;
Line 25, "sin" should be -- skin --;
Line 50, "ever" should be -- even --.

<u>Column 4,</u>
Line 19, "capable of being heated" should be deleted;
Line 20, after "means" should be inserted -- capable of being heated --.

<u>Column 5,</u>
Line 14, "or" should be -- for --.

<u>Column 6,</u>
Line 21, "elevate" should be -- elevated --.

Signed and Sealed this

Twenty-sixth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,726,683 B1
APPLICATION NO. : 05/730221
DATED : April 27, 2004
INVENTOR(S) : Shaw It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 1,826 days Delete the phrase "Subject to any disclaimer, the term of this patent is extended or adjusted under 35 USC 154(b) by 1,826 days"

and insert -- This patent application was filed prior to June 8, 1995, thus, no Patent Term Extension or Adjustment applies. --

Signed and Sealed this

Thirtieth Day of June, 2009

JOHN DOLL
*Acting Director of the United States Patent and Trademark Office*